US009790157B2

(12) United States Patent
Limburg et al.

(10) Patent No.: US 9,790,157 B2
(45) Date of Patent: Oct. 17, 2017

(54) RUTHENIUM-PHENOL CATALYSTS AND METHOD OF PREPARING MENTHONE FROM ISOPULEGOL

(71) Applicant: BASF SE, Ludwigshafen (DE)

(72) Inventors: Carolin Limburg, Mannheim (DE); Rocco Paciello, Bad Dürkheim (DE)

(73) Assignee: BASF SE (REITSTÖTTER, KINZEBACH & PARTNER), Ludwigshafen (DE)

( * ) Notice: Subject to any disclaimer, the term of this patent is extended or adjusted under 35 U.S.C. 154(b) by 0 days.

(21) Appl. No.: 15/123,271

(22) PCT Filed: Mar. 4, 2015

(86) PCT No.: PCT/EP2015/054453
§ 371 (c)(1),
(2) Date: Sep. 2, 2016

(87) PCT Pub. No.: WO2015/132275
PCT Pub. Date: Sep. 11, 2015

(65) Prior Publication Data
US 2017/0066704 A1 Mar. 9, 2017

(30) Foreign Application Priority Data
Mar. 5, 2014 (EP) .................... 14157826

(51) Int. Cl.
C07C 45/00 (2006.01)
C07C 45/51 (2006.01)
B01J 31/02 (2006.01)
B01J 31/22 (2006.01)
C07F 15/00 (2006.01)

(52) U.S. Cl.
CPC ......... C07C 45/512 (2013.01); B01J 31/0202 (2013.01); B01J 31/223 (2013.01); B01J 31/2226 (2013.01); B01J 31/2234 (2013.01); C07F 15/0046 (2013.01); B01J 2231/44 (2013.01); B01J 2231/641 (2013.01); B01J 2231/643 (2013.01); B01J 2231/645 (2013.01); B01J 2531/821 (2013.01); C07C 2601/14 (2017.05)

(58) Field of Classification Search
USPC ........................ 556/136, 140, 141
See application file for complete search history.

(56) References Cited

U.S. PATENT DOCUMENTS

| 2,785,188 A | 3/1957 | Coe |
| 2,885,444 A | 5/1959 | Fookes et al. |
| 3,247,262 A | 4/1966 | Kaeding |
| 4,097,461 A | 6/1978 | Rutledge |
| 4,134,919 A | 1/1979 | Yamanaka et al. |
| 4,380,676 A | 4/1983 | Rasberger |
| 7,960,593 B2 * | 6/2011 | Gralla ............... C07C 29/172 568/830 |
| 9,029,605 B2 * | 5/2015 | Schaub ............... C07C 45/002 568/361 |
| 2006/0160719 A1 | 7/2006 | Emura et al. |
| 2013/0281696 A1 | 10/2013 | Schaub et al. |
| 2013/0324770 A1 | 12/2013 | Schaub et al. |
| 2013/0331607 A1 | 12/2013 | Schaub et al. |
| 2014/0018570 A1 | 1/2014 | Pazicky et al. |
| 2014/0018574 A1 | 1/2014 | Raith et al. |
| 2014/0024833 A1 | 1/2014 | Schelwies et al. |
| 2014/0024854 A1 | 1/2014 | Schaub et al. |

FOREIGN PATENT DOCUMENTS

| DE | 4236111 A1 | 4/1994 |
| EP | 2706054 A1 | 3/2014 |
| WO | WO-2004056728 A1 | 7/2004 |
| WO | WO-2008016855 A1 | 2/2008 |
| WO | WO-2015086578 A1 | 6/2015 |

OTHER PUBLICATIONS

Zhang; Chemical Communications; 2013, 49, 8797-8799.*
U.S. Appl. No. 15/102,659, National phase of/see WO2015086578, Schwartztrauber et al.
Bhattacharya, S., et al., "Periodic Trends in Charge Distribution for Transition-Metal Complexes Containing Catecholate and Semiquinone Ligands. Synthetic, Physical, and Stereodynamic Properties of the Tris(3,5-di-tert-butylquinone) Complexes of Ruthenium and Osmium", Journal of the American Chemical Society, vol. 112, No. 3, (1990), pp. 1088-1096.
Brunner, H., et al., "Enantioselective Catalysis; 150: [1] Chiral-at-Metal ($\eta^6$-p-Cymene)Ruthenium(II) Complexes of Binaphthyl Ligands—Synthesis, Characterization, and Enantioselective Catalysis", Synthesis 2003, No. 7, (2003), pp. 1091-1099.
Gladiali, S., et al., "Asymmetric transfer hydrogenation: chiral ligands and applications", Chemical Society Reviews, vol. 35, No. 3, (2006), pp. 226-236.
Hanyu, A., et al., "Selective Aerobic Oxidation of Primary Alcohols Catalyzed by a Ru(PPh$_3$)$_3$Cl$_2$/Hydroquinone System", Tetrahedron Letters, vol. 39, No. 31, (1998), pp. 5557-5560.
Hartwig, J., et al., "Synthesis and Chemistry of Ruthenium Hydrido Aryloxides and Arylamides. An Investigation of Structure, N—H and O—H Elmination Processes, Proton-Catalyzed Exchage Reactions, and Relative Ru-X Bond Strengths", Organometallics, vol. 10, No. 6, (1991), pp. 1875-1887.
International Preliminary Report on Patentability with Annexes for PCT/EP2015/054453 mailed Jun. 2, 2016.
International Preliminary Report on Patententability with Annexes for PCT/EP2015/054693 mailed Jul. 4, 2016.

(Continued)

Primary Examiner — Pancham Bakshi
(74) Attorney, Agent, or Firm — Drinker Biddle & Reath LLP

(57) ABSTRACT

The present invention is directed towards a catalyst which is obtainable by contacting in situ a ruthenium precursor and a phenol derivative. Furthermore, the present invention is directed towards the use of said catalyst in transfer hydrogenation reactions. In particular, the present invention is directed to a method for preparing menthone starting from isopulegol.

8 Claims, No Drawings

(56) References Cited

OTHER PUBLICATIONS

International Search Report for PCT/EP2015/054453 mailed May 15, 2015.
International Search Report for PCT/EP2015/054693 mailed Apr. 29, 2015.
Koelle, U., et al., "Bis(phenol) Adduct of Cp*Ru($\eta^5$-oxocyclohexadienyl), a Doubly Symmetrical Hydrogen-Bridged Ruthenium Complex", Organometallics, vol. 10, No. 8, (1991), pp. 2573-2577.
Kondo, T., et al., "Synthesis, Structure, and Reactivity of Novel Ruthenium(II) Phenolate Complexes", Organometallics, vol. 24, No. 5, (2005), pp. 905-910.
Munshi, P., et al., "Hydrogenation of Carbon Dioxide Catalyzed by Ruthenium Trimethylphosphine Complexes: The Accelerating Effect of Certain Alcohols and Amines", Journal of the American Chemical Society, vol. 124, No. 27, (2002), pp. 7963-7971.
Panichakul, D., et al., "A Rare $\eta^3$ Binding Mode of Aryloxides in Iridium, Rhodium, and Ruthenium Complexes", Organometallics, vol. 27, No. 24, (2008), pp. 6390-6392.
Yildiz, E., et al., "Synthesis of Ru(III) and Al(III) Complexes Containing Anthraquinone Moiety and Interactions of the UV Radiations", Asian Journal of Chemistry, vol. 21, No. 5, (2009), pp. 4047-4053.
Zhang, L., et al., "Ru-catalyzed 1,4-addition of arylboronic acids to acrylic acid derivatives in the presence of phenols", Chemical Communications, vol. 49, No. 78, (2013), pp. 8797-8799.

\* cited by examiner

RUTHENIUM-PHENOL CATALYSTS AND METHOD OF PREPARING MENTHONE FROM ISOPULEGOL

CROSS-REFERENCE TO RELATED APPLICATIONS

This application is a national stage application (under 35 U.S.C. §371) of PCT/EP2015/054453, filed Mar. 4, 2015, which claims benefit of European Application No. 14157826.0, filed Mar. 5, 2014, both applications of which are incorporated herein by reference in their entirety.

The present invention is directed towards a catalyst which is obtainable by contacting in situ a ruthenium precursor and a phenol derivative. Furthermore, the present invention is directed towards the use of said catalyst in transfer hydrogenation reactions. In particular, the present invention is directed to a method for preparing menthone starting from isopulegol.

BACKGROUND OF THE INVENTION

Ruthenium transfer hydrogenation catalysts are known in the literature. These ruthenium catalysts all require specific ligands (e.g. phosphine, NHC-ligands, bipyridine ligands). The recycling behaviour of these ruthenium catalysts is not optimal. Their activity (Turnover frequency: TOF) diminishes with the increase of recycling-cycles and a high turnover number (TON) and thus a long life-cycle cannot be achieved.

Thus, ruthenium catalysts with improved characteristics are still needed. In particular, ruthenium catalysts which are readily accessible and with a long lifetime are highly desirable.

Ruthenium phenolate complexes have been reported in the literature. The synthesis of ruthenium phenolate complexes is described by Kondo at al. in Organometallics 2005, 24, 905-910. A ruthenium phenolate complex was prepared by reacting Ru($\eta^6$-COT)(dmfm)$_2$ with phenol. The resulting complex was isolated.

Panichakul et al., Organometallics 2008, 27, 6390-6392 describes the synthesis of BINOLate complexes of ruthenium. Said BINOLate complexes were prepared by reacting [RuCl$_2$-p-cymene]$_2$ with BINOL and isolated.

However, said ruthenium phenolate complexes are neither readily accessible nor has their use as catalysts been described.

Koelle at al., Organometallics 1991, 10, 2573-2577 describes the synthesis and structure of a bis(phenol) adduct of Cp*Ru($\eta^5$-oxocyclohexadienyl) (Cp*=$\eta^5$–C$_5$Me$_5$). Catalytic properties have not been described.

Bhattacharya et al., J. Am. Chem. Soc. 1990, 112, 1088-1096 describes the synthesis of tris(3,5-di-tert-butylquinone) complexes of ruthenium. Their periodic trends in charge distribution have been investigated. Catalytic properties have not been described.

Yildiz at al., Asian Journal of Chemistry 2009, 21 (5), 4047-4053 describes Ru(III) complex compounds of alizarin. The use of these complexes as UV absorbers was investigated. Catalytic properties have not been described.

Treibs et al, Ber. Dtsch. Chem. Gas. 1927, 60B, 2335-2341, describes the gas phase synthesis of menthone starting from isopulegol by using a copper catalyst. Under these conditions significant amounts of thymol (35%) have been observed. Menthone was obtained as a not clearly identified mixture of L-menthone and D-isomenthone. Ni-catalysts, which may be used for the dehydrogenation of menthol to menthone, lead to the elimination of water from isopulegol.

The problem to be addressed by the present invention is to provide a catalyst, suitable for transfer hydrogenation reactions, which is readily accessible, preferably obtainable from a commercially available starting material, which can be used in low concentrations and having a long lifetime.

It is a further object of the invention to provide a catalyst suitable for transfer hydrogenation reactions, which lead to high selectivity and high yield of the transfer hydrogenation product.

It is a further object of the Invention to provide an improved method for preparing menthone.

SUMMARY OF THE INVENTION

The above problems have been solved according to the invention by providing a ruthenium catalyst which is obtainable in situ in a liquid medium, which may be the liquid reaction medium.

In particular, the above problems has been solved by providing a ruthenium catalyst which is obtainable by contacting in situ in a liquid medium a ruthenium precursor which has labile ligands and as further ligand a phenol derivative of formula (I)

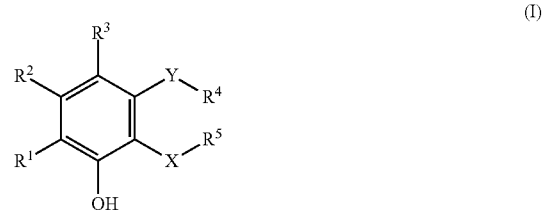

wherein
$R^1$, $R^2$, $R^3$ independently are hydrogen, alkyl, or hydroxy;
Y is a chemical bond, optionally substituted alkylene, optionally substituted arylene, —O—, or —S—;
$R^4$ is hydrogen, alkyl, hydroxy or optionally substituted aryl; or
$R^3$, Y—$R^4$ together with the carbon atoms to which they are bound form an anellated aromatic ring;
X is a chemical bond, optionally substituted alkylene, optionally substituted arylene, —O—, or —S—; and
$R^5$ is hydrogen, alkyl, hydroxy, or an optionally substituted aryl, or
$R^5$, $R^4$ together are optionally substituted arylene.

Preferably said ruthenium precursor does not possess strong donor ligands such as nitrogen or phosphorous donor ligands.

The ruthenium catalyst according to the invention is useful to catalyse transfer hydrogenation reactions, in particular dehydrogenation/hydrogenation reactions.

The present invention further provides a method for preparing menthone wherein a dehydrogenation/hydrogenation reaction is carried out in the liquid phase using isopulegol, a ruthenium precursor which has labile ligands and a phenol derivative of formula (I) as defined above.

The catalyst according to the Invention shows at least one of the following advantages:
Increased activity of the catalyst (high TOF);
Low concentrations of the catalyst are needed;
High yields and selectivity of the transfer hydrogenation product can be obtained.

DETAILED DESCRIPTION OF THE INVENTION a) General Definitions

"In situ" describes that the ruthenium catalyst is prepared in the liquid medium such as the liquid reaction medium without isolation of the catalytic species.

"Liquid medium" refers to an organic substance or a mixture of organic substances which are in the liquid state under the following conditions: T in the range from 100 to 220° C., preferably 150 to 200° C., more preferably 170 to 190° C.; p in the range of 1 to 100 bar, preferably 1 to 50 bar, more preferably 1 to 10 bar.

Normal pressure is preferred, but overpressure can be adjusted to keep reaction components in the liquid phase.

"Ruthenium precursor" refers to a ruthenium compound which allows the coordination of phenols, i.p. of such of formula (I) above. In particular, "ruthenium precursor" refers to ruthenium compounds which possess "labile" ligands. The ruthenium precursors do not possess strong donor ligands such as nitrogen and phosphorous donor-ligands (in particular trivalent N and trivalent P ligands and N-heterocyclic carbene ligands). Examples of such compounds are trialkylamines, trialkylphosphines, triarytphosphines, phosphonites, phosphites, pyridines, 1,3-bis(alkyl)imidazol-2-ylidenes and 1,3-bis(alkyl)imidazol-2-ylidenes.

"Labile" refers to the relative ability of the ligands to remain coordinated to the transition metal complex. Non-limiting examples of labile ligands are halides, alkyl, olefins (e.g. methylallyl, cyclooctadien, cyclooctatetraene, bicyclo[2.2.1]hepta-2,5-diene), hydrogen, or aromatic residues in particular aryl (e.g. benzene or p-cymene).

"Halogen" denotes fluorine, chlorine, bromine, iodine.

"Halide" denotes fluoride, chloride, bromide, iodide.

"Alkyl" represents a linear or branched alkyl group having 1 to 20, preferably 1 to 10 carbon atoms. Examples thereof are: $C_1$-$C_4$-alkyl radicals selected from methyl, ethyl, prop-1-yl, prop-2-yl, but-1-yl, but-2-yl, 2-methyl-prop-1-yl, or 2-methylprop-2-yl, or $C_1$-$C_{10}$-alkyl radicals selected from $C_1$-$C_4$-alkyl radicals as defined above and additionally pent-1-yl, 1-methylbut-1-yl, 2-methylbut-1-yl, 3-methytbut-1-yl, 2,2-dimethylprop-1-yl, 1-ethylprop-1-yl, hex-1-yl, 1,1-dimethylprop-1-yl, 1,2-dimethylprop-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl, 1-ethyl-2-methylprop-1-yl, hept-1-yl, oct-1-yl, non-1-yl, or dec-1-yl.

"Substituted alkyl" is an alkyl group as defined herein substituted with 1, 2, 3, 4 or 5 substituents, in particular 1, 2 or 3 substituents, preferably one substituent, which are independently selected from the group consisting of halogen, alkyl, substituted alkyl, cycloalkyl, aryl, and OH.

"Alkylene" represents a linear or branched divalent hydrocarbon group having 1 to 8 carbon atoms, preferably 1 to 4 as for example $C_1$-$C_4$-alkylene groups, like —$CH_2$—, —$(CH_2)_2$—, —$CH(CH_3)$—, and —$C(CH_3)_2$—.

"Substituted alkylene" Is an alkylene group as defined herein substituted with 1, 2 or 3 substituents, preferably one substituent, which are independently selected from the group consisting of halogen, alkyl, substituted alkyl, cycloalkyl, aryl, and OH.

"Cycloalkyl" represents a 3- to 12-membered, in particular 3- to 6-membered cycloaliphatic radical. Examples thereof are $C_3$-$C_{12}$-cycloalky such as cyclopropyl, cyclobutyl, cyclo-pentyl and cyclohexyl. The cyclic structure may be unsubstituted or may carry 1, 2, 3 or 4 $C_1$-$C_4$ alkyl radicals, preferably one or more methyl radicals.

"Aliphatic olefins" are $C_2$-$C_{12}$-like $C_2$-$C_4$-olefins, such as ethylene, propene, but-1-ene, but-2-ene, 2-methylprop-1-ene, "Substituted aliphatic olefins" are aliphatic olefins as defined herein, substituted by 1, 2 or 3 substituents, preferably one substituent, which are independently selected from the group consisting of halogen, alkyl, substituted alkyl, cycloalkyl, aryl, and OH.

"Cyclic olefins" are $C_3$-$C_{20}$-, like $C_3$-$C_8$- or $C_4$-$C_{12}$-cyclic olefins, such as cyclopropene, cyclobutene, cyclobutadiene, cyclopentadlene, cyclohexene, cyclohexadiene, cyclooctene, cyclooctadiene;

"Substituted cyclic olefins" are cyclic olefins as defined herein, substituted by 1, 2 or 3 substituents, preferably one substituent, which are independently selected from the group consisting of halogen, alkyl, substituted alkyl, cycloalkyl, aryl, and OH.

"Aryl" represents a 6- to 12-membered, in particular 6- to 10-membered, aromatic cyclic radical. Examples thereof are: $C_6$-$C_{12}$-aryl such as phenyl and naphthyl.

"Substituted aryl" is an aryl group as defined herein substituted with 1, 2, 3, 4, or 5 substituents, in particular 1, 2, 3 substituents, preferably one or two substituents, which are independently selected from the group consisting of halogen, alkyl, substituted alkyl, alkoxy and OH.

"Arylene" represents a 6- to 12-membered, in particular 6- to 10-membered aromatic cyclic diradical. Examples thereof are: $C_6$-$C_{12}$-arylene such as 1,2-phenylene and 2,3-naphthylene.

"Substituted arylene" is an arylene group as defined herein substituted with 1, 2, 3 substituents, preferably one substituent, which are independently selected from the group consisting of halogen, alkyl, substituted alkyl, alkoxy and OH.

"Alkoxy" represents a radical of the formula R—O—, wherein R is a linear or branched alkyl group having from 1 to 6, in particular 1 to 4 carbon atoms. Examples thereof are $C_1$-$C_6$-alkoxy radicals selected from methoxy, ethoxy, n-propoxy, isopropoxy, n-butoxy, 2-butoxy, iso-butoxy (2-methylpropoxy), tert-butoxy pentyloxy, 1-methylbutoxy, 2 methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4 methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Carbonyl is $>C=O$.

"1,3-Dialkyldionate" denotes the anion of 1,3-dialkylcarbonyl of general formula R—C(O)—$CH_2$—C(O)—R, wherein R is an alkyl radical having from 1 to 6, preferably from 1 to 4, carbon atoms as defined herein. Examples thereof are 1,3-di-$C_1$-$C_4$-alkyl-dionate such as acetylacetonate and 2,2,6,6-tetramethyl-3,5-heptanedionate.

"Alkanoate" represents a radical R—C(O)—O, wherein R is an alkyl radical having from 1 to 6, preferably from 1 to 4, carbon atoms as defined herein. Examples thereof are $C_1$-$C_4$-alkanoate such as acetate Abbreviations used herein include the following:

COD=cyclooctadien; COT=cyclooctatetraene; NBD=bycyclo[2.2.1]hepta-2,5-dien (Norbomadlene); acac=acetylacetonate, dmfm=dimethyl fumarate.

Compounds with at least one asymmetric carbon atom as mentioned herein encompass, unless otherwise stated, any isomeric form thereof.

If not otherwise stated the term menthone refers to anyone of the possible stereoisomers such as:

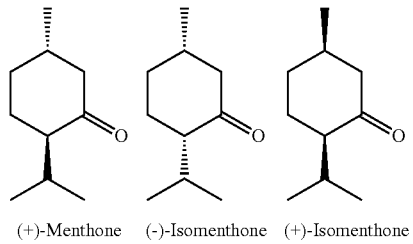

(+)-Menthone   (−)-Isomenthone   (+)-Isomenthone

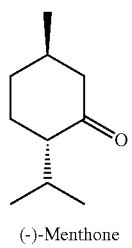

(−)-Menthone

If not otherwise stated the term isopulegol refers to anyone of the possible stereoisomers such as:

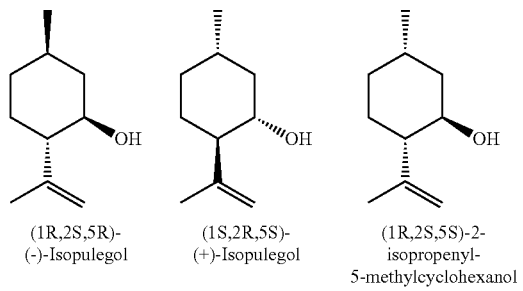

(1R,2S,5R)-   (1S,2R,5S)-   (1R,2S,5S)-2-
(−)-Isopulegol   (+)-Isopulegol   isopropenyl-
5-methylcyclohexanol

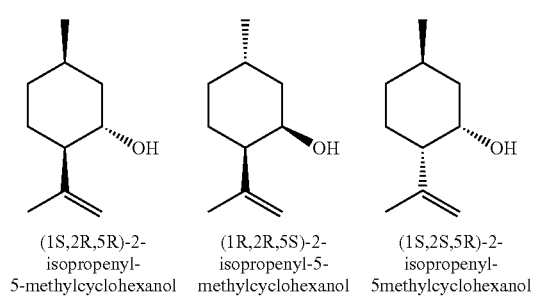

(1S,2R,5R)-2-   (1R,2R,5S)-2-   (1S,2S,5R)-2-
isopropenyl-   isopropenyl-5-   isopropenyl-
5-methylcyclohexanol   methylcyclohexanol   5methylcyclohexanol

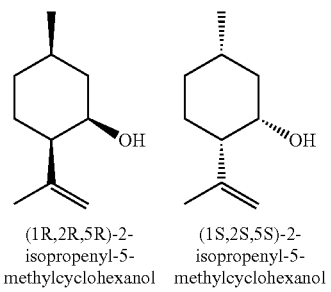

(1R,2R,5R)-2-   (1S,2S,5S)-2-
isopropenyl-5-   isopropenyl-5-
methylcyclohexanol   methylcyclohexanol b) Particular Embodiments of the Invention The present invention relates in particular to the following embodiments:

1. A ruthenium catalyst which is obtainable by contacting in situ in a liquid medium a ruthenium precursor which has labile ligands and a phenol derivative of formula (I)

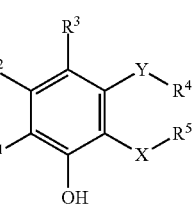

(I)

wherein $R^1$, $R^2$, $R^3$ independently are hydrogen, alkyl, like $C_1$-$C_{10}$-alkyl (e.g. methyl, tertbutyl, nonyl) or hydroxy;

Y is a chemical bond, optionally substituted alkylene like $C_1$-$C_6$-alkylene (e.g. —C(Me$_2$)-), optionally substituted arylene like optionally substituted phenylene, (e.g. 1,2-phenylene), —O—, or S—;

$R^4$ is hydrogen, alkyl, like $C_1$-$C_{10}$-alkyl (e.g. methyl), hydroxy or optionally substituted aryl, like optionally substituted phenyl, (e.g. phenyl), or $R^3$, Y—$R^4$ together with the carbon atoms to which they are bound form an anellated aromatic ring;

X is a chemical bond, optionally substituted alkylene, like $C_1$-$C_6$-alkylene (e.g. —CH$_2$—), optionally substituted arylene like optionally substituted phenylene, (e.g. 1,2-phenylene), —O—, or S—, and $R^5$ is hydrogen, alkyl, like $C_1$-$C_{10}$-alkyl (e.g. methyl, tertbutyl, nonyl), hydroxy, or an optionally substituted aryl, like optionally substituted $C_6$-$C_{12}$-aryl, (e.g. phenyl, 2-hydroxy-phenyl, 2-hydroxy-3,5-dimethyl-phenyl, 2-hydroxy-3,5-ditertbutyl-phenyl, 2-hydroxynaphthyl), or $R^5$, $R^4$ together are optionally substituted arylene, like optionally substituted phenylene, (e.g. 4-methyl-6-hydroxy-1,2-phenylene).

2. The ruthenium catalyst of embodiment 1 wherein the phenol derivative has one of the formulae

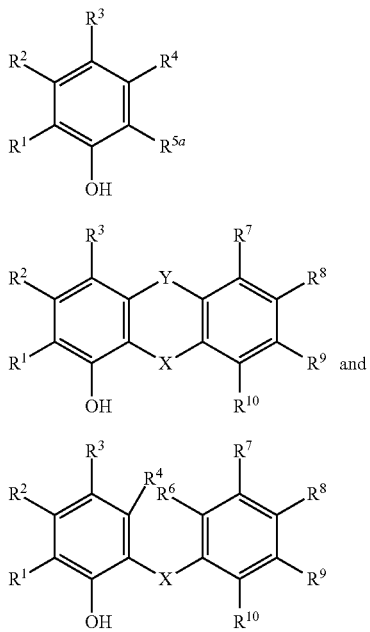

wherein
R¹, R², R³, R⁴ independently are hydrogen, alkyl, like $C_1$-$C_{10}$-alkyl (e.g. methyl, tertbutyl, nonyl), or hydroxy, or
R³, R⁴ together with the carbon atoms to which they are bound form an anellated aromatic ring (e.g. phenyl);
$R^{5a}$ is hydrogen, alkyl, like $C_1$-$C_{10}$-alkyl (e.g. methyl, tertbutyl, nonyl), or hydroxy;
Y is a chemical bond, optionally substituted alkylene, like $C_1$-$C_8$-alkylene (e.g. —CMe₂-), optionally substituted arylene, like optionally substituted phenylene (e.g. 1,2-phenylene), —O—, or —S—;
R⁶, R⁷, R⁸, R⁹ independently are hydrogen or alkyl, like $C_1$-$C_{10}$-alkyl (e.g. methyl, tertbutyl, nonyl), or
R⁶, R⁷ together with the carbon atoms to which they are bound form an anellated aromatic ring (e.g. phenyl);
R¹⁰ is hydrogen or hydroxy, and
X is a chemical bond, optionally substituted alkylene, like $C_1$-$C_8$-alkylene (e.g. —CMe₂-), optionally substituted arylene like optionally substituted phenylene (e.g. 1,2-phenylene), —O—, or —S—.

3. The ruthenium catalyst of embodiment 2 wherein
R¹, R², R³, R⁴ independently are hydrogen, branched or linear alkyl, like $C_1$-$C_{10}$-alkyl (e.g. tBu, Me, nonyl), or hydroxy, or
R³, R⁴ together with the carbon atoms to which they are bound form an anellated aromatic ring (e.g. phenyl);
$R^{5a}$ is hydrogen, branched or linear alkyl, like $C_1$-$C_{10}$-alkyl (e.g. tBu, Me), or hydroxy;
Y is a chemical bond or optionally substituted alkylene, like $C_1$-$C_6$-alkylene (e.g. —CMe₂-), preferably optionally substituted alkylene (e.g. —CMe₂-);
R⁶, R⁷, R⁸, R⁹ independently are hydrogen or branched or linear alkyl, like $C_1$-$C_{10}$-alkyl (e.g. tBu, Me), or
R⁶, R⁷ together with the carbon atoms to which they are bound form an anellated aromatic ring (e.g. phenyl);
R¹⁰ is hydrogen or hydroxy, and
X is a chemical bond, optionally substituted alkylene, like optionally substituted phenylene (e.g. —CH₂—), or —O—.

For formulae (Ia), (Ib) and (Ic) according to embodiments 2 and 3 the following meanings are particularly mentioned:
R¹, R³ independently are hydrogen, linear or branched alkyl, like $C_1$-$C_{10}$-alkyl (e.g. methyl, tertbutyl, nonyl), or hydroxy.
R² is hydrogen or linear or branched alkyl, like $C_1$-$C_{10}$-alkyl (e.g. methyl, tertbutyl, nonyl), in particular hydrogen or methyl.
R⁴ is hydrogen or linear or branched alkyl, like $C_1$-$C_{10}$-alkyl (e.g. methyl, tertbutyl, nonyl), in particular hydrogen, or R³, R⁴ together with the carbon atoms to which they are bound form an anellated aromatic ring, in particular a phenyl ring.
R⁶ is hydrogen or linear or branched alkyl, like $C_1$-$C_{10}$-alkyl (e.g. methyl, tertbutyl, nonyl), in particular hydrogen.
R⁷, R⁹ independently are hydrogen, linear or branched alkyl, like $C_1$-$C_{10}$-alkyl (e.g. methyl, tertbutyl, nonyl), or R⁷, R⁶ together with the carbon atoms to which they are bound form an anellated aromatic ring, in particular a phenyl ring.
R⁸ is hydrogen or linear or branched alkyl, like $C_1$-$C_{10}$-alkyl (e.g. methyl, tertbutyl, nonyl), in particular hydrogen or methyl.

4. The ruthenium catalyst of any of the previous embodiments wherein the phenol derivative has formula (Ia)

wherein R¹, R², R³, R⁴ and $R^{5a}$ independently are hydrogen, alkyl, like $C_1$-$C_{10}$-alkyl, or hydroxy.

In the phenol derivatives of formula (Ia), the following meanings are particularly mentioned:
R¹, R³ independently are hydrogen, linear $C_1$-$C_{10}$-alkyl (e.g. methyl, nonyl), branched $C_3$-$C_{10}$-alkyl (e.g. tertbutyl), or hydroxy.
R² is hydrogen, linear $C_1$-$C_{10}$-alkyl (e.g. methyl, nonyl), or branched $C_3$-$C_{10}$-alkyl (e.g. tertbutyl), in particular hydrogen.
R⁴ is hydrogen, linear $C_1$-$C_{10}$-alkyl (e.g. methyl, nonyl), or branched $C_3$-$C_{10}$-alkyl (e.g. tertbutyl), in particular hydrogen.
$R^{5a}$ is hydrogen, linear $C_1$-$C_{10}$-alkyl (e.g. methyl, nonyl), branched $C_3$-$C_{10}$-alkyl (e.g. tertbutyl), or hydroxy.

5. The ruthenium catalyst of embodiment 1 or 2 wherein the phenol derivative has formula (Ib)

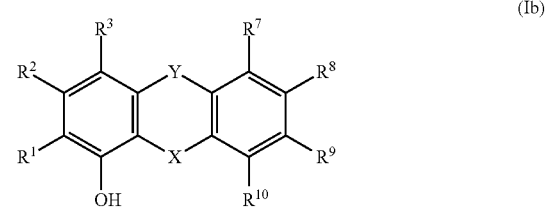

wherein

R$^1$, R$^2$, R$^3$ independently are hydrogen or alkyl.

Y is a chemical bond, optionally substituted alkylene, like C$_1$-C$_8$-alkylene (e.g. —CMe$_2$-), optionally substituted arylene, like optionally substituted phenylene, —O—, or —S—;

R$^7$, R$^8$, R$^9$ independently are hydrogen or alkyl, like C$_1$-C$_{10}$-alkyl;

R$^{10}$ is hydrogen or hydroxy, and

X is a chemical bond, optionally substituted alkylene, like C$_1$-C$_8$-alkylene (e.g. —CMe$_2$-), optionally substituted arylene, like optionally substituted phenylene, —O—, or —S—.

6. The ruthenium catalyst of embodiment 5 wherein in the phenol derivative of formula (Ib)

R$^1$, R$^2$, R$^3$ independently are hydrogen, linear C$_1$-C$_{10}$-alkyl, or branched C$_3$-C$_{10}$-alkyl;

Y is optionally substituted alkylene, preferably alkylene like C$_1$-C$_8$-alkylene, (e.g. —CMe$_2$-);

R$^7$, R$^8$, R$^9$ independently are hydrogen, linear C$_1$-C$_{10}$-alkyl, or branched C$_3$-C$_1$-alkyl;

R$^{10}$ is hydrogen or hydroxy, and

X is —O—.

In the phenol derivatives of formula (Ib) according to embodiments 5 and 6 the following meanings are particularly mentioned:

R$^1$, R$^3$ are hydrogen.

R$^2$ is hydrogen, linear C$_1$-C$_{10}$-alkyl (e.g. methyl, nonyl), or branched C$_3$-C$_{10}$-alkyl (e.g. tertbutyl), in particular methyl.

R$^7$, R$^9$ are hydrogen.

R$^8$ is hydrogen, linear C$_1$-C$_{10}$-alkyl (e.g. methyl, nonyl), or branched C$_3$-C$_{10}$-alkyl (e.g. tertbutyl), in particular methyl.

7. The ruthenium catalyst of embodiments 1 or 2 wherein the phenol derivative has formula (Ic)

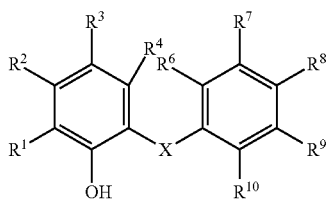

(Ic)

wherein

R$^1$, R$^2$, R$^3$, R$^4$ independently are hydrogen or alkyl, like C$_1$-C$_{10}$-alkyl, or R$^3$, R$^4$ together with the carbon atoms to which they are bound form an anellated aromatic ring, preferably a phenyl ring;

R$^6$, R$^7$, R$^8$, R$^9$ independently are hydrogen or alkyl, like C$_1$-C$_{10}$-alkyl, or R$^6$, R$^7$ together with the carbon atoms to which they are bound form an anellated aromatic ring, preferably a phenyl ring;

R$^{10}$ is hydrogen or hydroxy, and

X is a chemical bond, optionally substituted alkylene, like C$_1$-C$_8$-alkylene (e.g. —CH$_2$—), optionally substituted arylene, like optionally substituted phenylene, —O—, or —S—.

8. The ruthenium catalyst of embodiment 7, wherein in the phenol derivative of formula (Ic)

R$^1$, R$^2$, R$^3$, R$^4$ independently are hydrogen, linear C$_1$-C$_{10}$-alkyl, or branched C$_3$-C$_{10}$-alkyl, or R$^3$, R$^4$ together with the carbon atoms to which they are bound form an anellated aromatic ring, preferably a phenyl ring;

R$^6$, R$^7$, R$^8$, R$^9$ independently are hydrogen, linear C$_1$-C$_{10}$-alkyl, or branched C$_3$-C$_{10}$-alkyl, or R$^6$, R$^7$ together with the carbon atoms to which they are bound form an anellated aromatic ring, preferably a phenyl ring;

R$^{10}$ is hydrogen or hydroxy, and

X is a chemical bond or alkylene, like C$_1$-C$_8$-alkylene (e.g. —CH$_2$—).

In the phenol derivatives of formula (Ic) according to embodiments 7 and 8 the following meanings are particularly mentioned:

R$^2$ is hydrogen.

R$^4$ is hydrogen, or R$^4$, R$^3$ together with the carbon atoms to which they are bound form an anellated aromatic ring, preferably a phenyl ring.

R$^6$ is hydrogen, or R$^6$, R$^7$ together with the carbon atoms to which they are bound form an anellated aromatic ring, preferably a phenyl ring.

R$^8$ is hydrogen.

9. The ruthenium catalyst of any one of previous embodiments wherein the phenol derivative of formula (I) is selected from among the compounds:

3,3',5,5'-tetra-tert-butyl-(1,1'-biphenyl)-2,2'-diol;
nonylphenol;
2,2'-biphenol;
2-benzylphenol;
2,4-di-tert-butylphenol;
2,6-di-tert-butylphenol;
phenol;
hydroquinone;
2,6-di-tert-butyl-4-methylphenol;
4',5,5'-tetramethyl-2,2'biphenol, and
(R)-(+)-1,1'-bi(2-naphtol).

Preferably the phenol derivative of formula (I) is nonyl phenol, 2,2'-biphenol, or 3,3',5,5'-tetra-tert-butyl-(1,1'-biphenyl)-2,2'-diol.

10. The ruthenium catalyst of any of the previous embodiments wherein the ruthenium precursor which has labile ligands is represented by the formula (II)

$$[RuL_m]_n \qquad (II)$$

wherein

Ru is in the oxidation state (+II), (+III) or (+IV);

each ligand L independently is hydride, halide (e.g. Cl, Br, I), alkyl, like C$_1$-C$_{10}$-alkyl, optionally substituted aliphatic olefins like C$_2$-C$_{12}$-olefins, (e.g. methyl allyl, 2,4-dimethylpentadienyl, 2,7-dimethyl-2,6-octadiene, dodecatriene), optionally substituted cyclic olefins, like C$_4$-C$_{10}$-cyclic olefins, (e.g. cyclooctadiene, cyclopentadienyl, pentamethyicycopentadienyl), —CO, 1,3-dialkyldionate (e.g. acetylacetonate, 2,2,6,6-tetramethyl-3,5-heptanedionate), alkanoate, like C$_1$-C$_6$-alkanoate, (e.g. acetate), or optionally substituted aryl (e.g. benzene, p-cymene);

m is an integer in a range from 2 to 6;

n is at least 1, or a salt thereof.

11. The ruthenium catalyst of any of the preceding embodiments, wherein R$^4$ is different from hydroxy, when Y represents —O— or —S— and R$^5$ is different from hydroxy, when X represents —O— or —S—.

12. The ruthenium catalyst of any of the preceding embodiments, wherein the ruthenium precursor does not possess strong donor ligands, in particular nitrogen or phosphorous donor ligands, in particular trivalent nitrogen or trivalent phosphorous donor ligands or N-heterocyclic carbene donor ligands; non-limiting examples of such "strong donor ligands" are trialkylamines, trialkylphosphines, triarylphosphines, phosphites, phosphonites, 1,3-bis(aryl)imidazol-2-ylidenes, 1,3-bis(alkyl)imidazol-2-ylidenes or pyridines, in particular trimethylphosphine, tricyclohexylphosphine, triphenylphosphine, triethylphosphite, diethylmethylphosphonite, triethylamine, triphenylamine, tetramethylethylenediamine, pyridine, 2,2'-bipyridine, 1,3-di-t-butylimidazol-2-ylidene or 1,3-bis(2,6-di-i-propylphenyl)4,5-dihydroimidazol-2-ylidine.

13. The ruthenium catalyst of any of the preceding embodiments, wherein the phenol derivative of formula I, Ia, Ib or Ic does not possess strong donor substituents, in particular nitrogen or phosphorous donor substituents; non-limiting examples of such "strong donor substituents" are dimethylphosphanyl, diphenylphosphanyl, dicyclohexylphosphanyl, diethoxyphosphanyl, diethylamino, diphenylamino, dimethylamino, methylamino, pyridyl and 2,2'-bipyridyl substituents.

14. The ruthenium catalyst of any of the preceding embodiments, wherein
   optionally substituted alkylene represents alkylene optionally substituted by 1, 2 or 3 substituents which are independently selected from the group consisting of halogen, alkyl, substituted alkyl, cycloalkyl, aryl, and OH;
   optionally substituted arylene represents arylene optionally substituted by 1, 2, 3 substituents which are independently selected from the group consisting of halogen, alkyl, substituted alkyl, alkoxy and OH;
   optionally substituted aryl represents aryl optionally substituted by 1, 2, 3, 4 or 5 substituents, in particular 1, 2, 3 substituents which are independently selected from the group consisting of halogen, alkyl, substituted alkyl, alkoxy and OH;
   optionally substituted aliphatic olefins represents aliphatic olefins optionally substituted by 1, 2 or 3 substituents which are independently selected from the group consisting of halogen, alkyl, substituted alkyl, cycloalkyl, aryl, and OH; and
   optionally substituted cyclic olefins represents cyclic olefins optionally substituted by 1, 2 or 3 substituents which are independently selected from the group consisting of halogen, alkyl, substituted alkyl, cycloalkyl, aryl, and OH.

15. The ruthenium catalyst of any of the previous embodiments wherein the ruthenium in the ruthenium precursor is in the oxidation state (+II), (+III) or (+IV).

16. The ruthenium catalyst of any of the previous embodiments wherein the labile ligands of the ruthenium precursor are independently selected from the group consisting of hydride, halide (e.g. Cl, Br, I), alkyl like $C_1$-$C_{10}$-alkyl, optionally substituted aliphatic olefins like $C_2$-$C_{12}$-olefins, (e.g. methyl allyl, 2,4-dimethylpentadienyl, 2,7-dimethyl-2,6-octadiene, dodecatriene), optionally substituted cyclic olefins like $C_4$-$C_{10}$-cyclic olefins, (e.g. cyclooctadiene, cyclopentadienyl, pentamethylcyclopentadienyl), —CO, 1,3-dialkyldionate (e.g. acetatonate, 2,2,6,6-tetramethyl-3,5-heptanedionate), alkanoate like $C_1$-$C_6$-alkanoate, (e.g. acetate), or optionally substituted aryl (e.g. benzene, p-cymene).

17. The ruthenium catalyst of any of the previous embodiments wherein the ruthenium precursor is selected from among the compounds:
Bis(2,4-dimethylpentadienyl)ruthenium(II);
Bis(2-methylallyl)(1,5-cyclooctadiene)ruthenium(II);
Bis(2,2,6,6-tetramethyl-3,5-heptanedionato)(1,5-cyclooctadiene)ruthenium(II);
Chloro(1,5-cyclooctadiene)(pentamethylcyclopentadienyl)ruthenium(II);
Chloro(pentamethylcyclopentadienyl)ruthenium(II) tetramer;
Cyclopentadienyl(p-cymene)ruthenium(II) hexafluorophosphat;
Dicarbonylcyclopentadienylruthenium(II) dimer,
Dichloro(benzene)ruthenium(II);
Di-μ-chlorobis[(p-cymene)chlororuthenium(II)];
Dichloro(1,5-cyclooctadiene)ruthenium(II);
Dichlorotricarbonytruthenium (dimer);
Dichloro(pentamethylcyclopentadienyl)ruthenium(III) polymer;
Ruthenium(III) acetylacetonate;
Ruthenium(III) bromide;
Ruthenium(III) chloride;
Ruthenium(III) iodide;
Acetatodicarbonylruthenium(IV) polymer,
Ammonium hexachlororuthenate(IV);
Dichloro(μ-chloro)bis[(1,2,3,6,7,8-η)-2,7-dimethyl-2,6-octadien-1,8-dlyl]diruthenium(IV); or
Dichloro(2,6,10-dodecatriene-1,12-diyl)ruthenium(IV).

18. The ruthenium catalyst of any of the previous embodiments wherein the ruthenium in the ruthenium precursor is in the oxidation state (+II) or (+III).

19. The ruthenium catalyst of any of the previous embodiments wherein the ruthenium precursor is bis(2-methylallyl)(1,5-cyclooctadiene)ruthenium(II), dichloro(1,5-cyclooctadiene)ruthenium(II), ruthenium(II) acetylacetonate or ruthenium chloride(III).

20. The ruthenium catalyst of any of the previous embodiments wherein the ruthenium precursor is bis(2-methylallyl)(1,5-cyclooctadiene)ruthenium(III) or ruthenium(III) acetylacetonate.

21. The use of the ruthenium catalyst of any of the previous embodiments in transfer hydrogenation reactions.

22. The use of the ruthenium catalyst of any of the previous embodiments wherein the transfer hydrogenation reaction is the isomerization of unsaturated alcohols, the isomerization of unsaturated carbonyl, the hydrogenation of alkenes, the hydrogenation of ketones, the dehydrogenation of alcohols, a dehydrogenating esterification, the dehydrogenating coupling of alcohols with amines to amides, the alkylation of amines with alcohols, or the oxidation of alcohols to aldehydes.

23. The use of the ruthenium catalyst of any of the previous embodiments wherein the transfer hydrogenation reaction is the isomerization of unsaturated alcohols, the isomerization of unsaturated aldehydes, the hydrogenation of alkenes, the hydrogenation of ketones, or the dehydrogenation of alcohols.

24. The use of the ruthenium catalyst of any of the previous embodiments wherein the transfer hydrogenation reaction is the isomerization of unsaturated alcohols (i.p. the preparation of menthone from isopulegol).

25. A method for preparing menthone wherein a dehydrogenation/hydrogenation reaction is carried out in the liquid phase using isopulegol, a ruthenium precursor according to any one of embodiments 10 to 16 and a phenol derivative of formula (I) according to any one of embodiments 1 to 9.

26. The method according to embodiment 25, wherein the amount of ruthenium in the ruthenium catalyst of any one of claims 1 to 16 is in the range from 50 to 3000, preferably 100 to 1000, more preferably is 200 to 600 ppm by weight based on the total liquid reaction mixture in the reaction space.

27. The method according to embodiment 25 or 26, wherein the weight ratio between the phenol derivative and isopulegol is in the range from 1:1 to 1:20.
   Preferably the weight ratio between the phenol derivative and isopulegol is 1:10.

28. The method according to any one of embodiments 25 to 27, wherein the reaction is carried out at a temperature in the range from 100 to 220° C., preferably 150 to 200° C. More preferably, the reaction is carried out at a temperature in the range from 170 to 190° C.

C. Further Embodiment of the Invention a) Reactants

The ruthenium precursors are commercially available or can be easily prepared following standard chemistry. See for example J. Powell, B. L. Shaw, J. Chem. Soc. A: Inorganic, Physical, Theoretical 1968, 1, 159-161; M. O. Albers, E. Singleton, J. E. Yates, Inorg. Synthesis 1989, 26, 249-258; R. Grobelny, B. Jezowska-Trzeblatowska, W. Wojchiechowski J. Inorg. Nucl. Chem. 1966, 28, 2715-2718; A. Endo, K. Shimizu, G. P. Satô, M. Mukaida Chem. Lett. 1984, 437-440.

The phenol derivatives of formula (I) are commercially available or can be easily prepared following standard chemistry. See for example U.S. Pat. No. 4,380,676, U.S. Pat. No. 4,097,461, U.S. Pat. No. 2,885,444, U.S. Pat. No. 2,785,188 and U.S. Pat. No. 3,247,262.

b) Transfer Hydrogenation Reactions

The use of ruthenium catalysts in transfer hydrogenation reactions has been described in the following reviews: T. Naota, H. Takaya and S. Murahashi, Chem. Rev. 1998, 98, 2599-2660; S. Bähn, S. Imm, L. Neubert, M. Zhang, H. Neumann and M. Beller, ChemCatChem 2011, 3, 1853; C. Gunanathan and D. Milstein Science, 2013, 341, 1229712-1-1229812-12.

The ruthenium catalyst according to the invention is used in transfer hydrogenation reactions such as the isomerization of unsaturated alcohols, the isomerization of unsaturated carbonyl, the hydrogenation of alkenes, the hydrogenation of ketones, the dehydrogenation of alcohols, a dehydrogenating esterification, the dehydrogenating coupling of alcohols with amines to amides, the alkylation of amines with alcohols, or the oxidation of alcohols to aldehydes.

In the isomerization of unsaturated alcohols compounds comprising at least a double or triple bond and a primary or secondary alcohol are heated in presence of a catalyst according to the invention.

Representative non limiting examples of isomerization of alcohols are shown in the scheme below:

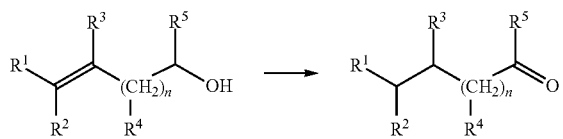

-continued

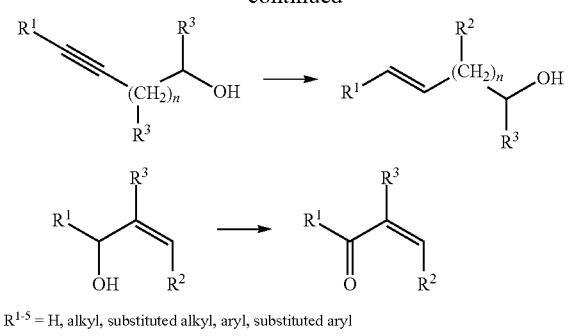

$R^{1-5}$ = H, alkyl, substituted alkyl, aryl, substituted aryl
n > 1

Hydrogenation of alkenes is performed in presence of a suitable hydrogen source and the catalyst according to the invention. Representative non limiting examples of alkene hydrogenations are reported in the scheme below.

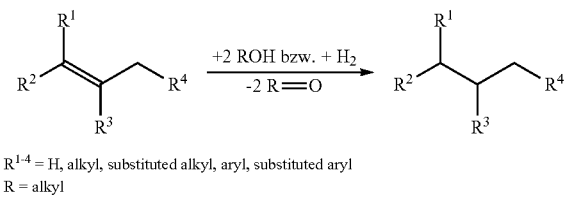

$R^{1-4}$ = H, alkyl, substituted alkyl, aryl, substituted aryl
R = alkyl

Hydrogenation of ketones or aldehydes is performed in presence of a suitable hydrogen source and the catalyst according to the Invention. Representative non limiting examples of ketone hydrogenations are reported in the scheme below.

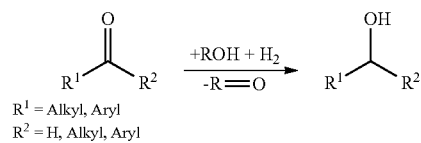

$R^1$ = Alkyl, Aryl
$R^2$ = H, Alkyl, Aryl

In the alkylation of amines with alcohols compounds comprising at least a primary or secondary alcohol are reacted with a primary amine in presence of the catalyst according to the Invention. Representative non limiting examples of alkylations of amines with alcohols are reported in the scheme below.

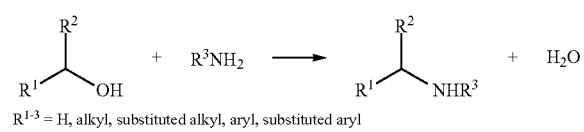

$R^{1-3}$ = H, alkyl, substituted alkyl, aryl, substituted aryl

In the dehydrogenating coupling of alcohols with amines to amides compounds comprising at least a primary alcohol are reacted with a primary amine in presence of the catalyst according to the Invention. Representative non limiting examples of dehydrogenating coupling of alcohols with amines are reported in the scheme below.

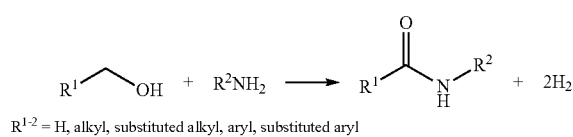
$R^{1-2}$ = H, alkyl, substituted alkyl, aryl, substituted aryl

In a dehydrogenating esterification compounds comprising at least one primary alcohol are reacted with a further primary or secondary alcohol in presence of the catalyst according to the Invention. Representative non limiting examples of dehydrogenating esterifications are reported in the scheme below.

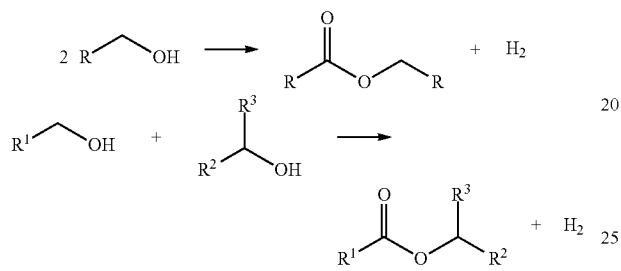

R = H, alkyl, substituted alkyl, aryl, substituted aryl
$R^{1-3}$ = H, alkyl, substituted alkyl, aryl, substituted aryl The Invention is illustrated by the following non-limiting examples:

EXPERIMENTAL SECTION

General Information

In the following examples the following definitions apply:
"Inert conditions": All experiments and manipulations were carried out under an atmosphere of argon. The weighing of all starting materials was done in a nitrogen purged glovebox. Reactions and further manipulations were performed using standard schlenk techniques.

"Semi-inert condition": When weighing the starting materials no special precautions were taken. Inertization of the reaction vessel equipped with the starting material was done by applying vacuum and ventilating with argon for 3 times. Reactions and further manipulations were than carried out under an atmosphere of argon using standard Schlenk techniques.

"Ambient pressure"=1070 mbar
The following ruthenium precursors A and B were used:
A=Bis(2-methylallyl)(1,5-cylcooctadiene)ruthenium(II).
B=Ruthenium(III) acetyl acetonate (Ruacac).
The following phenol derivatives 1 to 11 were used:

TABLE 1

| 1 | 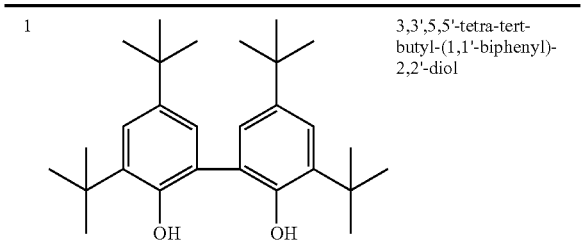 | 3,3',5,5'-tetra-tert-butyl-(1,1'-biphenyl)-2,2'-diol |

TABLE 1-continued

| 2 | Nonyl-C6H4-OH | Nonylphenol |
| 3 | 2,2'-biphenol structure | 2,2'-Biphenol |
| 4 | 2-benzylphenol structure | 2-Benzylphenol |
| 5 | 2,4-di-tert-butylphenol structure | 2,4-Di-tert-butylphenol |
| 6 | 2,6-di-tert-butylphenol structure | 2,6-Di-tert-butylphenol |
| 7 | phenol structure | Phenol |
| 8 | hydroquinone structure | Hydroquinone |
| 9 | 2,6-di-tert-butyl-4-methylphenol structure | 2,6-Di-tert-butyl-4-methylphenol |

TABLE 1-continued

| | | |
|---|---|---|
| 10 | 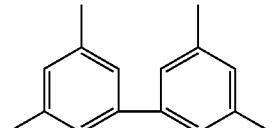 | 4,4',5,5'-Tetramethyl-2,2'Biphenol |
| 11 | 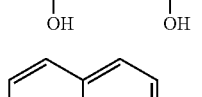 | (R)-(+)-1,1'-Bi(2-naphtol) |

Example 1: Isomerization of Unsaturated Alcohols—Isopulegol to Menthone/Isomenthone

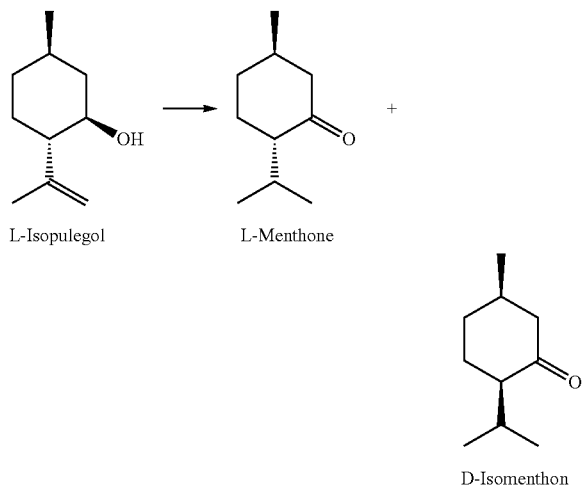

Analytical Method:

GC analyses were performed using an Agilent 6890 equipped with a VF-23ms column (60 m, 0.25 mm, 0.25 µm).

Temperature program: 90° C., 2 min isotherm
3 K/min to 120° C., 2 min isotherm
20 K/min to 240° C., 10 min isotherm
Constant Flow: 3 ml/min
Carrier gas: Hydrogen
Internal Standard: Decane Using enantiomerically pure L-isopulegol as starting material the reactions described below gave enantiomerically pure L-menthone and D-isomenthone. The term "menthone yield" in the following examples is therefore defined as the sum of the yield of L-menthone and the yield of D-isomenthone. The term "menthone selectivity" is defined as sum of the selectivity L-menthone and the selectivity D-isomenthone.

Menthol and pulegone are intermediates in the isomerization of isopulegol and will react further to form menthone or rather isomenthone by increasing the reaction time or the reaction temperature. This is therefore not to be regarded as a loss of the starting material isopulegol. Unless otherwise stated, menthol and pulegone will both be included in the total selectivity listed below.

("Total selectivity"=selectivity of menthone+selectivity of isomenthone+selectivity of pulegone+ selectivity of menthol).

The following individual examples and comparative examples 1.1 to 1.38 were performed to illustrate said isomerization reaction:

Comparative Example 1.1-1.7:
Ruthenium-Phosphanyl-Complexes as Catalyst

The ruthenium-phosphanyl-complexes were synthesized according to the literature (S. P. Nolan, T. R. Belderrain and R. H. Grubbs *Organometallics* 1997, 16, 5569-5571).

Under inert conditions the ruthenium-phosphanyl-complex and 9 g isopulegol were placed in a 30 ml Schlenk-flask equipped with a magnetic stirring bar. At ambient pressure the mixture was heated at 180° C. and stirred for the reaction time $t_1$. Conversion and menthone yield were determined via calibrated GC analysis. The results are summarized in the Table 2 below.

TABLE 2

| Example | Catalyst | m(Ru) [ppm] | $t_1$ [h] | Conversion [%] | Total* Selectivity [%] | Menthone yield [%] |
|---|---|---|---|---|---|---|
| 1.1 | [Ru(P"Oct$_3$)$_4$(H)$_2$] | 2000 | 2 | 45.2 | 58.7 | 15.8 |
| | | | 4 | 100 | 91.3 | 63.9 |
| | | | 6 | 100 | 92.3 | 84.9 |
| 1.2 | [Ru(PCyhex$_3$)$_4$(H)$_2$] | 2000 | 2 | 32.1 | 82.5 | 23.5 |
| | | | 4 | 38.9 | 82.1 | 28.2 |
| | | | 6 | 40.2 | 80.3 | 28.1 |
| 1.3 | [Ru(P"Bu$_3$)$_4$(H)$_2$] | 2000 | 18 | 42.4 | 67.5 | 14.2 |
| | | | 42 | 56.7 | 53.5 | 14.3 |
| 1.4 | [Ru(CO)(P"Bu$_3$)$_3$(H)$_2$] | 2000 | 18 | 92.0 | 75.4 | 22.6 |
| | | | 42 | 99.8 | 81.7 | 35.1 |
| 1.5 | [Ru(dcpe)$_2$(H)$_2$] | 2000 | 2 | 100 | 84.9 | 39.3 |
| | | | 4 | 100 | 90.8 | 87.9 |
| | | | 6 | 100 | 88.8 | 85.4 |
| 1.6 | [Ru(dppbutyl)$_2$(H)$_2$] | 2000 | 2 | 56.8 | 69.4 | 28.3 |
| | | | 4 | 83.3 | 82.8 | 32.3 |
| | | | 6 | 91.8 | 87.8 | 36.3 |
| 1.7 | [Ru(dppbenzyl)$_2$(H)$_2$] | 2000 | 18 | 86.8 | 75.5 | 25.1 |
| | | | 42 | 100 | 82.7 | 46.9 | wherein dcpe is

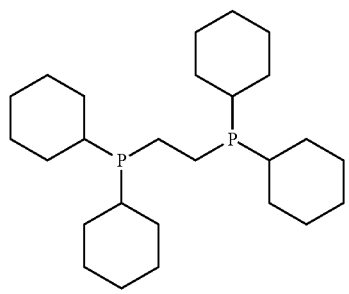 [SMILES: C1CCC(P(CCP(C2CCCCC2)C2CCCCC2)C2CCCCC2)CC1]

dppbutyl is

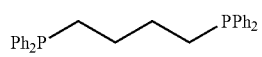

dppbenzyl is

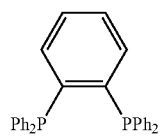

Example 1.8: Ruthenium Precursor A and Phenol Derivative 1 as Catalyst

Under semi-inert conditions 9 g Isopulegol, 76 mg A (=2000 ppm [Ru]) and 3 g of the phenol derivative 1 were placed in a 30 ml Schlenk-flask equipped with a magnetic stirring bar. At ambient pressure the mixture was heated at 180° C. and stirred for 4 hours. Conversion and menthone yield were determined via calibrated GC analysis. The results are summarized in the Table 3 below.

Comparative Example 1.9: Ruthenium Precursor A as Catalyst

Under semi-inert conditions 12 g Isopulegol and 76 mg A (=2000 ppm [Ru]) were placed in a 30 ml Schlenk-flask equipped with a magnetic stirring bar. At ambient pressure the mixture was heated at 180° C. and stirred for 4 hours. Conversion and menthone yield were determined via calibrated GC analysis. In the absence of phenol precipitation of ruthenium black is observed, illustrating the essential role of the phenol for avoiding catalyst loss i.e. for improving catalyst recycling. The results are summarized in the Table 3 below.

Comparative Example 1.10: No Addition of Catalyst

Under semi-inert conditions 12 g isopulegol were placed in a 30 ml Schlenk-flask equipped with a magnetic stirring bar. At ambient pressure the mixture was heated at 180° C. and stirred for 18 hours. Conversion and menthone yield were determined via calibrated GC analysis. The results are summarized in the Table 3 below.

TABLE 3

| Example | Catalyst | m(Ru) [ppm] | $t_1$ [h] | Conversion [%] | Total Selectivity [%] | Menthone yield [%] |
|---|---|---|---|---|---|---|
| 1.1 | [Ru(P″Oct$_3$)$_4$(H)$_2$] | 2000 | 2 | 45.2 | 58.7 | 15.8 |
|  |  |  | 4 | 100 | 91.3 | 63.9 |
|  |  |  | 6 | 100 | 92.3 | 84.9 |
| 1.5 | [Ru(dcpe)$_2$(H)$_2$] | 2000 | 2 | 100 | 84.9 | 39.3 |
|  |  |  | 4 | 100 | 90.8 | 87.9 |
|  |  |  | 6 | 100 | 88.8 | 85.4 |
| 1.8 | A + 1 | 2000 | 2 | 100 | 87.9 | 78.9 |
|  |  |  | 4 | 100 | 88.0 | 81.0 |
| 1.9 | A * | 2000 | 2 | 100 | 91.3 | 72.4 |
|  |  |  | 4 | 100 | 91.5 | 76.3 |
| 1.10 | No catalyst | — | 18 | 15.2 | 6.0 | 0.0 |

* Ruthenium „black" precipitates during the reaction

Example 1.11: Ruthenium Precursor A and Phenol Derivative 1 as Catalyst

Under semi-inert conditions 102 g isopulegol, 106.4 mg A (=300 ppm [Ru]) and 10.1 g of the phenol derivative 1 were placed in a 250 ml Schlenk-flask equipped with a magnetic stirring bar. At ambient pressure the mixture was heated at 180° C. and stirred for 4 hours. The reaction mixture was allowed to cool down to room temperature before conversion and menthone yield were determined via calibrated GC analysis. Full-conversion of 100% could be obtained and a menthone yield of 95.4% was determined in the crude product. (menthone selectivity=90.3%; pulegone selectivity=1.4%; menthol selectivity=0%; total selectivity=91.7%)

For catalyst separation the reaction mixture was distilled at 1 mbar and 60° C. overhead temperature. 96.4 g distillation product could be obtained. GC analysis of the product gave a composition of 1.3 wt % menthol, 1.5 wt. % pulgone, 1.7 wt. % unknown by-products, 53.3 wt % L-menthone and 42.2 wt % D-isomenthone giving an isolated menthone yield of 90% (=92 g menthone+isomenthone)

Examples 1.12-1.18: Ruthenium Precursor A and Phenol Derivatives 2-6, 9 or 11 as Catalyst Under semi-inert conditions 9 g isopulegol, 9.5 mg A (=300 ppm [Ru]) and 1 g of the phenol derivative were placed in a 30 ml Schlenk-flask equipped with a magnetic stirring bar. At ambient pressure the mixture was heated at 180° C. and stirred for reaction time $t_1$. Conversion and menthone yield were determined via calibrated GC analysis. The results are summarized in the Table 4 below.

TABLE 4

| Example | Phenol derivative | $t_1$ [h] | Conversion [%] | Total Selectivity [%] | Menthone yield [%] |
|---|---|---|---|---|---|
| 1.12 | 2 | 6 | 100 | 93.8 | 80.3 |
| 1.13 | 3 | 6 | 65.3 | 92.6 | 46.5 |
| 1.14 | 4 | 6 | 66.1 | 93.9 | 40.2 |
| 1.15 | 5 | 6 | 100 | 97.4 | 72.4 |
| 1.16 | 6 | 6 | 100 | 100 | 85.8 |
| 1.17 | 9 | 6 | 34.5 | 100 | 24.3 |
| 1.18 | 11 | 4 | 100 | 97.5 | 94.5 |

Examples 1.19-1.25: Ruthenium Precursor A and Phenol Derivatives 3-9 as Catalyst Under semi-inert conditions 9 g isopulegol, 9.5 mg A (=300 ppm [Ru]) and 1 g of the phenol derivative were placed in a 30 ml Schlenk-flask equipped with a magnetic stirring bar. At ambient pressure the mixture was heated at 160'C and stirred for reaction time $t_1$. Conversion and menthone yield were determined via calibrated GC analysis. The results are summarized in the Table 5 below.

TABLE 5

| Example | Phenol derivative | $t_1$ [h] | Conversion [%] | Total Selectivity [%] | Menthone yield [%] |
|---|---|---|---|---|---|
| 1.19 | 3 | 6 | 22.9 | 100 | 14.8 |
| 1.20 | 4 | 6 | 73.1 | 100 | 61.5 |
| 1.21 | 5 | 6 | 83.9 | 100 | 73.1 |
| 1.22 | 6 | 4 | 100 | 97.4 | 73.6 |
| 1.23 | 7 | 4 | 100 | 96.8 | 84.3 |
| 1.24 | 8 | 4 | 46.1 | 86.4 | 33.9 |
| 1.25 | 9 | 4 | 100 | 97.4 | 70.5 |

Examples 1.26-1.29: Ruthenium Precursor B and Phenol Derivatives 1-3 and 10 as Catalyst Under semi-inert conditions 9 g isopulegol, 11.8 mg B and 1 g of the phenol derivative were placed in a 30 ml Schlenk-flask equipped with a magnetic stirring bar. At ambient pressure the mixture was heated at 180° C. and stirred for the reaction time $t_1$. Conversion and menthone yield were determined via GC analysis. The results are summarized in the Table 6 below.

TABLE 6

| Example | Phenol derivative | $t_1$ [h] | Conversion [%] | Total Selectivity [%] | Menthone yield [%] |
|---|---|---|---|---|---|
| 1.26 | 1 | 4 | 100 | 89.1 | 73.8 |
| 1.27 | 2 | 4 | 100 | 84.8 | 79.6 |
| 1.28 | 3 | 4 | 77.8 | 95.1 | 60.5 |
| 1.29 | 10 | 4 | 47.5 | 93.4 | 30.6 |

Comparative Example 1.30 and 1.31: Catalyst Recycling Experiments

Under inert conditions the ruthenium-phosphanyl-complex and isopuelgol were placed in a 100 ml Schlenk-flask equipped with a magnetic stirring bar. At ambient pressure the mixture was heated at 180° C. and stirred for the reaction time $t_1$. The reaction mixture was then distilled (p=1 mbar, overhead temperature=55-60° C.) in order to separate the catalyst and the reaction products. The latter was analyzed by calibrated GC chromatography in order to determine the conversion and menthone yield. Isopulegol was then added to the catalyst containing distillation residue and the reaction was repeated. 5 catalyst recycles were carried out for each catalyst. The examples show that the catalysts of the invention compared to the phosphanyl-substituted ruthenium complexes are recyclable. One can see very clearly that the turn over frequency of the claimed catalysts is well above that of the phosphanyl catalysts. The selectivity and yield of menthone is also improved.

Example 1.32-1.35: Catalyst Recycling Experiments

Under semi-inert conditions Isopulegol, A or rather B and the phenol derivative 1, 2 or 3 were placed in a 100 ml Schlenk-flask equipped with a magnetic stirring bar. At ambient pressure the mixture was heated at 180° C. and stirred for the reaction time $t_1$. The reaction mixture was than distilled (p=1 mbar, overhead temperature=55-60° C.) in order to separate the catalyst and the reaction products. The latter was analyzed by calibrated GC chromatography in order to determine the conversion and menthone yield. Isopulegol were then added to the catalyst containing distillation residue and the reaction was repeated. 5 catalyst recycles were carried out for each catalyst.

The results of the catalyst recycling experiments are summarized in the Table 7 below:

TABLE 7

| Example | 1.30 | | | | | 1.31 | | | | | 1.32 | | | | |
|---|---|---|---|---|---|---|---|---|---|---|---|---|---|---|---|
| Cat. | [Ru(dcpe)$_2$(H)$_2$] | | | | | [Ru(P"Oct$_3$)$_4$(H)$_2$] | | | | | A + 1 | | | | |
| Recycle | 1 | 2 | 3 | 4 | 5 | 1 | 2 | 3 | 4 | 5 | 1 | 2 | 3 | 4 | 5 |
| m (Isopulegol) [g] | 18.9 | 19.0 | 19.0 | 47.6 | 18.7 | 26.0 | 28.6 | 24.9 | 25.1 | 24.9 | 15 | 15 | 15.1 | 16.1 | 15.6 |
| m (phenol derivate) [g] | | | — | | | | | — | | | | | 3 | | |
| m (Ru-complex) [mg] | | | 265 | | | | | 810 | | | | | 25.3 | | |
| m (Ru) in ppm | 1495 | 1486 | 1486 | 593 | 1510 | 1984 | 1804 | 2072 | 2055 | 2072 | 539 | 539 | 535 | 502 | 518 |
| $t_1$ [h] | 20 | 20 | 20 | 44 | 20 | 22 | 22 | 22 | 22 | 22 | 2 | 2 | 2 | 2 | 2 |
| TOF [h$^{-1}$] | 7 | 6 | 15 | 14 | 11 | 13 | 8 | 9 | 7 | 5 | 396 | 525 | 490 | 496 | 538 |
| TON | | | 1393 | | | | | 905 | | | | | 4888 | | |
| Total Sel. | 57.4 | 83.9 | 86.2 | 80.1 | 86.6 | 95.2 | 72.9 | 84.7 | 80.0 | 73.6 | 76.4 | 94.2 | 96.3 | 89.1 | 98.1 |
| Menthone yield [%] | 34.1 | 27.4 | 67.1 | 55.2 | 50.2 | 88.8 | 45.7 | 59.8 | 46.3 | 34.6 | 64.4 | 85.5 | 79.2 | 75.2 | 84.2 |

TABLE 7-continued

| Example | 1.33 | | | | | 1.34 | | | | | 1.35 | | | | |
|---|---|---|---|---|---|---|---|---|---|---|---|---|---|---|---|
| Cat. | A + 2 | | | | | B + 2 | | | | | B + 3 | | | | |
| Recycle | 1 | 2 | 3 | 4 | 5 | 1 | 2 | 3 | 4 | 5 | 1 | 2 | 3 | 4 | 5 |
| m (Isopulegol) [g] | 45 | 45 | 45 | 45 | 45 | 45 | 45 | 45 | 45 | 45 | 45 | 45 | 45 | 45 | 45 |
| m (phenol derivate) [g] | | 5 | | | | | 5 | | | | | 5 | | | |
| m (Ru-complex) [mg] | | 47 | | | | | 59 | | | | | 59 | | | |
| m (Ru) in ppm | 295 | 295 | 295 | 295 | 295 | 296 | 296 | 296 | 296 | 296 | 296 | 296 | 296 | 296 | 296 |
| $t_1$ [h] | 2 | 2 | 2 | 2 | 2 | 4 | 4 | 4 | 4 | 4 | 8 | 8 | 8 | 8 | 8 |
| TOF [$h^{-1}$] | 920 | 940 | 845 | 784 | 832 | 392 | 472 | 470 | 469 | 415 | 125 | 128 | 140 | 134 | 125 |
| TON | | | 8644 | | | | | 8872 | | | | | 5213 | | |
| Total Sel. [%] | 96.4 | 99.9 | 100 | 98.8 | 100 | 84.8 | 100 | 100 | 100 | 96.3 | 73.5 | 68.0 | 89.5 | 88.8 | 83.9 |
| Menthone yield [%] | 92.8 | 94.8 | 85.2 | 79.1 | 83.9 | 79.6 | 95.8 | 95.4 | 95.2 | 84.2 | 50.6 | 51.8 | 57.0 | 54.0 | 50.6 |

Comparative Example 1.36 Ruthenium Precursor A and Phenol Derivative 1 (Pre-Synthesized and Isolated Catalyst)

Under semi-inert conditions 0.5 g A and 1.93 g of the phenol derivative 1 were placed in a 30 ml Schlenk-flask equipped with a magnetic stirring bar. At ambient pressure the mixture was heated at 160° C. and stirred for 30 minutes. After cooling down to room temperature an orange-brown solid was obtained and purified by silica gel column chromatography using heptane as eluent. 38.2 mg (=300 ppm [Ru]) of the obtained greyish solid together with 9 g isopulegol were then placed in a 30 ml Schlenk-flask. At ambient pressure the mixture was heated at 180° C. and stirred for 4 hours. Conversion and menthone yield were determined via calibrated GC analysis. The results are shown in Table 8 below.

Comparative Example 1.37 Ruthenium Precursor A and Phenol Derivative 1 (Pre-Synthesized and Isolated Catalyst)

Under semi-inert conditions 0.1 g A and 384 mg of the phenol derivative 1 were placed in a 30 ml Schlenk-flask equipped with a magnetic stirring bar and were dissolved in 2 ml mesitylene. At ambient pressure the mixture was heated at 160° C. and stirred for 30 minutes. After cooling down to room temperature the orange-brown reaction mixture was filtered. The obtained light-brown solid was washed with mesitylene and dried in vacuum. 38.4 mg (=300 ppm [Ru]) of the obtained solid together with 9 g isopulegol were then placed in a 30 ml Schlenk-flask. At ambient pressure the mixture was heated at 180° C. and stirred for 4 hours. Conversion and menthone yield were determined via calibrated GC analysis. The results are shown in Table 8 below.

Comparative Example 1.38 Ruthenium Precursor A and Phenol Derivative 3 (Pre-Synthesized and Isolated Catalyst)

Under semi-inert conditions 0.2 g A and 350 mg of the phenol derivative 3 were placed in a 30 ml Schlenk-flask equipped with a magnetic stirring bar. At ambient pressure the mixture was heated at 160° C. and stirred for 30 minutes. After cooling down to room temperature an orange-brown solid was obtained. 14.3 mg (=300 ppm [Ru]) of the obtained solid together with 9 g isopulegol were then placed in a 30 ml Schlenk-flask under semi-inert conditions. At ambient pressure the mixture was heated at 180° C. and stirred for 4 hours. Conversion and menthone yield were determined via calibrated GC analysis. The results are shown in Table 8 below.

TABLE 8

Results of the experiments with pre-synthesized and isolated catalysts in comparison to example 1.8

| Example | $t_1$ [h] | Conversion [%] | Total Selectivity [%] | Menthone yield [%] |
|---|---|---|---|---|
| 1.8 | 4 | 100 | 88.0 | 81.0 |
| 1.36 | 4 | 2.5 | 78.9* | 0.0 |
| 1.37 | 4 | 2.8 | 71.0* | 0.0 |
| 1.38 | 4 | 11.6 | 75.3 | 5.3 |

*Yield of menthol = 2.0%; taking the very low conversion into account, the total selectivity is >70%.

Example 2: Hydrogenation of Unsaturated Bonds/Dehydrogenation of Alcohols

Example 2.1: 1-Octane to Octane

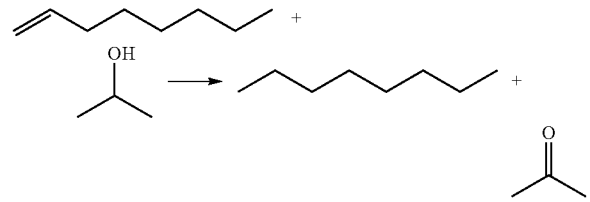

Analytical Method:

GC analyses were performed using an Agilent6890 equipped with an Optima-1 column (30 m, 0.32 mm, 0.5 µm).

Temperature program: 50° C., 2 min isotherm
5 K/min to 190° C., 5 min isotherm
20 K/min to 250° C., 17 min isotherm
Constant Flow: 0.8 ml/min
Carrier gas: Helium Under semi-inert conditions 0.5 g 1-octane, 5 g 2-propanol, 0.5 g 1 and 4.5 mg A were placed in a 50 ml glass autoclave equipped with a paddle stirrer. At inherent pressure the mixture was heated at 140° C. and stirred for 24 hours. A 1-octene conversion of 99% and an octane selectivity of 73% were determined via GC analysis.

Example 2.2: Pulegone to Menthone

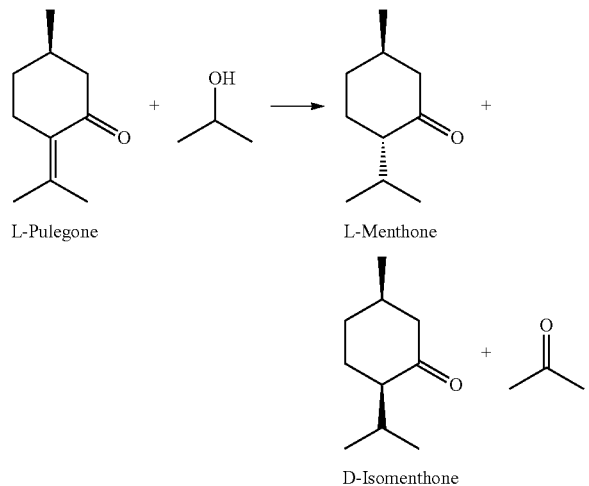

L-Pulegone → L-Menthone + D-Isomenthone

Analytical Method: (see example 1)

Under semi-inert conditions 1 g L-pulegone, 8 g 2-propanol, 1 g 1 and 9.5 mg A were placed in a 50 ml glass autoclave equipped with a paddle stirrer. At inherent pressure the mixture was heated at 180° C. and stirred for 5 hours. A L-pulegone conversion of 88% and a menthone selectivity of 93.6% were determined via calibrated GC analysis.

Example 2.3: Menthol+Pulegone to Menthone

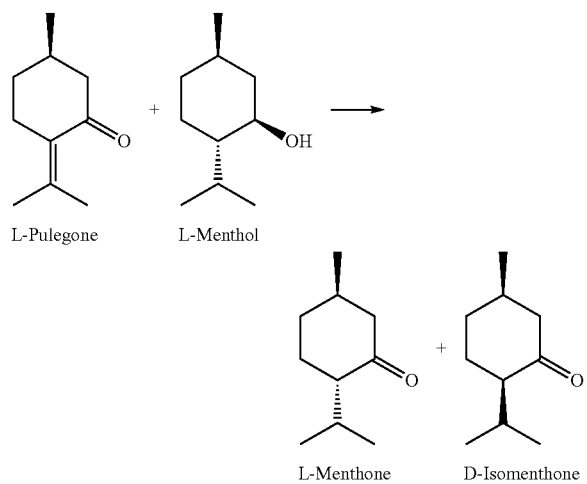

L-Pulegone + L-Menthol → L-Menthone + D-Isomenthone

Analytical Method: (see example 1)

Under semi-inert conditions 0.5 g L-menthol, 0.5 L-pulegone, 1 g 1 and 9.5 mg A were placed in a 50 ml Schlenk-flask equipped with a paddle stirrer. At ambient pressure the mixture was heated at 180° C. and stirred for 18 hours. A conversion of 76.5%, a menthone selectivity of 96.5% and a menthone yield of 73.9% were determined via calibrated GC analysis.

Example 3: Hydrogenation of Ketone/Dehydrogenation of Alcohols

Example 3.1: Butenone to 2-Butanol

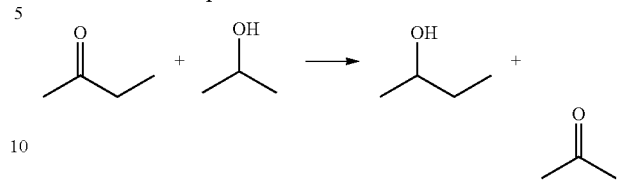

Analytical Method:

GC analyses were performed using an Agilent6890 equipped with an Optima-1 column (30 m, 0.32 mm, 0.5 μm).

Temperature program: 50° C., 2 min isotherm
5 K/min to 90° C., 5 min isotherm
20 K/min to 250° C., 17 min isotherm
Constant Flow: 0.8 ml/min
Carrier gas: Helium Under semi-inert conditions 0.5 g butanone, 7.9 g 2-propenol, 0.84 g 1 and 8.8 mg A were placed in a 50 ml glass autoclave equipped with a paddle stirrer. At inherent pressure the mixture was heated at 180° C. and stirred for 24 hours. A butanone conversion of 91.6% and a 2-butanol yield of 91.6% were determined via GC analysis.

Example 4: Amination of Alcohols

Example 4.1: Dihexylamine+Hexanol to Trihexylamine

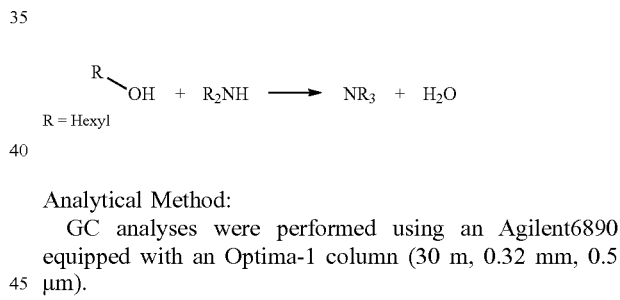

R = Hexyl

Analytical Method:

GC analyses were performed using an Agilent6890 equipped with an Optima-1 column (30 m, 0.32 mm, 0.5 μm).

Temperature program: 50° C., 5 min isotherm
20 K/min to 300° C., 42.5 min isotherm
Constant Flow: 0.8 m/min
Carrier gas: Helium Under semi-inert conditions 4.9 g dihexylamine, 3 g 1-hexanol, 1 g 1 and 9.5 mg A were placed in a 30 ml Schlenk-flask equipped with a magnetic stirring bar. At ambient pressure the mixture was heated at 180° C. and stirred for 8 hours. A 1-hexanol conversion of 21.3% and a trihexylamine yield of 18.2% were determined via GC analysis.

Example 4.2: Hexylamine+Hexanol to Dihexylamine

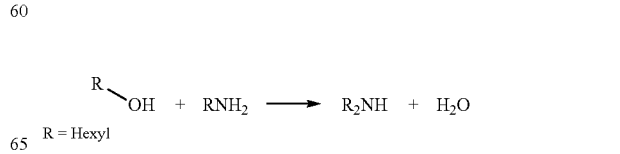

R = Hexyl

Analytical Method: (See Example 4.1)

Under semi-inert conditions 4.0 g hexylamine, 4.5 g 1-hexanol, 1 g 1 and 9.0 mg A were placed in a 30 ml Schlenk-flask equipped with a magnetic stirring bar. At ambient pressure the mixture was heated at 160° C. and stirred for 24 hours. A 1-hexanol conversion of 38.2% and a dihexylamine yield of 31.1% were determined via GC analysis.

The disclosure of any document referred to herein is Incorporated by reference.

The invention claimed is:

1. A method for preparing menthone comprising conducting a transfer hydrogenation reaction in the presence of a liquid medium that includes isopulegol, a ruthenium precursor and a phenol derivative,
wherein the phenol derivative:isopulegol is present at a weight ratio of 1:10, and the transfer hydrogenation reaction is carried out at a temperature in range from 150 to 200° C., and the phenol derivative is of the formulae (Ia) or (Ic)

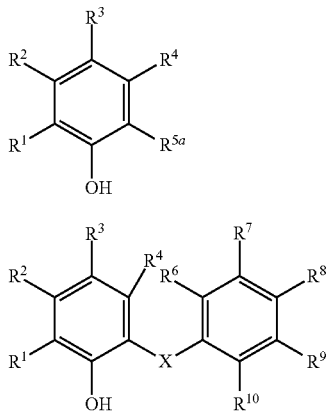

(Ia)

(Ic)

wherein
$R^1$, $R^2$, $R^3$, $R^4$ independently are hydrogen, alkyl, or hydroxy, or
$R^3$, $R^4$ together with the carbon atoms to which they are bound form an anellated aromatic ring;
$R^{5a}$ is hydrogen, alkyl, or hydroxy;
$R^6$, $R^7$, $R^8$, $R^9$ independently are hydrogen or alkyl, or
$R^6$, $R^7$ together with the carbon atoms to which they are bound form an anellated aromatic ring;
$R^{10}$ is hydrogen or hydroxy, and
X is a chemical bond; alkylene optionally substituted by 1, 2 or 3 substituents which are independently selected from the group consisting of halogen, alkyl, substituted alkyl, cycloalkyl, aryl, and OH; or arylene optionally substituted by 1, 2, 3 substituents which are independently selected from the group consisting of halogen, alkyl, substituted alkyl, alkoxy and OH; —O—; and —S—;
and the ruthenium precursor does not possess nitrogen or phosphorous donor ligands.

2. The method of claim 1 wherein
$R^1$, $R^2$, $R^3$, $R^4$ independently are hydrogen, branched or linear alkyl, or hydroxy, or
$R^3$, $R^4$ together with the carbon atoms to which they are bound form an anellated aromatic ring;
$R^{5a}$ is hydrogen, alkyl branched or linear alkyl, or hydroxy;
$R^6$, $R^7$, $R^8$, $R^9$ independently are hydrogen, or branched or linear alkyl, or
$R^6$, $R^7$ together with the carbon atoms to which they are bound form an anellated aromatic ring;
$R^{10}$ is hydrogen or hydroxy, and
X is a chemical bond, alkylene optionally substituted by 1, 2 or 3 substituents which are independently selected from the group consisting of halogen, alkyl, substituted alkyl, cycloalkyl, aryl, OH, or —O—.

3. The method of claim 1 wherein therein the phenol derivative is of the formula (Ia)

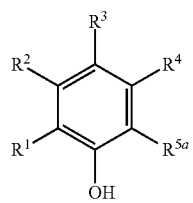

(Ia)

wherein $R^1$, $R^2$, $R^3$, $R^4$ and $R^{5a}$ independently are hydrogen, alkyl, or hydroxy.

4. The method of claim 1 wherein the phenol derivative is of the formula (Ic)

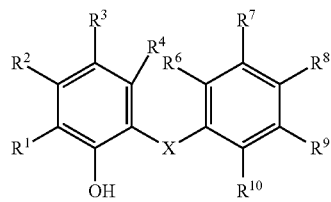

(Ic)

wherein
$R^1$, $R^2$, $R^3$, $R^4$ independently are hydrogen or alkyl, or
$R^3$, $R^4$ together with the carbon atoms to which they are bound form an anellated aromatic ring;
$R^6$, $R^7$, $R^8$, $R^9$ independently are hydrogen or alkyl, or
$R^6$, $R^7$ together with the carbon atoms to which they are bound form an anellated aromatic ring;
$R^{10}$ is hydrogen or hydroxy, and
X is a chemical bond; alkylene optionally substituted by 1, 2 or 3 substituents which are independently selected from the group consisting of halogen, alkyl, substituted alkyl, cycloalkyl, aryl, and OH; arylene optionally substituted by 1, 2, 3 substituents which are independently selected from the group consisting of halogen, alkyl, substituted alkyl, alkoxy and OH; —O—, or —S—.

5. The method of claim 4 wherein
$R^1$, $R^2$, $R^3$, $R^4$ independently are hydrogen, linear $C_1$-$C_{10}$-alkyl, or branched $C_3$-$C_{10}$-alkyl, or
$R^3$, $R^4$ together with the carbon atoms to which they are bound form an anellated aromatic ring;
$R^6$, $R^7$, $R^8$, $R^9$ independently are hydrogen, linear $C_1$-$C_{10}$-alkyl, or branched $C_3$-$C_{10}$-alkyl, or
$R^6$, $R^7$ together with the carbon atoms to which they are bound form an anellated aromatic ring;
$R^{10}$ is hydrogen or hydroxy, and
X is a chemical bond or alkylene.

6. The method of claim 1 wherein the ruthenium precursor having labile ligands is of formula (II) or a salt thereof $$[RuL_m]_n \quad (II)$$

wherein

Ru is in the oxidation state (+II), (+III) or (+IV);

each L independently is selected from the group consisting a. hydride;
b. halide;
c. alkyl;
d. aliphatic olefins optionally substituted by 1, 2 or 3 substituents which are independently selected from the group consisting of halogen, alkyl, substituted alkyl, cycloalkyl, aryl, and OH;
e. cyclic olefins optionally substituted by 1, 2 or 3 substituents which are independently selected from the group consisting of halogen, alkyl, substituted alkyl, cycloalkyl, aryl, and OH;
f. —CO;
g. 1,3-dialkyldionate;
h. alkanoate and
i. aryl optionally substituted by 1, 2, 3, 4 or 5 which are independently selected from the group consisting of halogen, alkyl, substituted alkyl, alkoxy and OH;

m is an integer in a range from 2 to 6;

n is at least 1.

7. The method of claim 5 wherein the ruthenium precursor having labile ligands is of formula (II) or a salt thereof $$[RuL_m]_n \quad (II)$$

wherein

Ru is in the oxidation state (+II), (+III) or (+IV);

each L independently is selected from the group consisting a. hydride;
b. halide;
c. alkyl;
d. aliphatic olefins optionally substituted by 1, 2 or 3 substituents which are independently selected from the group consisting of halogen, alkyl, substituted alkyl, cycloalkyl, aryl, and OH;
e. cyclic olefins optionally substituted by 1, 2 or 3 substituents which are independently selected from the group consisting of halogen, alkyl, substituted alkyl, cycloalkyl, aryl, and OH;
f. —CO;
g. 1,3-dialkyldionate;
h. alkanoate and
i. aryl optionally substituted by 1, 2, 3, 4 or 5 which are independently selected from the group consisting of halogen, alkyl, substituted alkyl, alkoxy and OH;

m is an integer in a range from 2 to 6;

n is at least 1.

8. The method of claim 1 wherein the ruthenium precursor is selected from the group consisting of Bis(2,4-dimethylpentadienyl)ruthenium(II);
Bis(2-methylallyl)(1,5-cyclooctadiene)ruthenium(II);
Bis(2,2,6,6-tetramethyl-3,5-heptanedionato)(1,5-cyclooctadiene)ruthenium(II);
Chloro(1,5-cyclooctadiene)(pentamethylcyclopentadienyl)ruthenium(II);
Chloro(pentamethylcyclopentadienyl)ruthenium(II) tetramer;
Cyclopentadienyl(p-cymene)ruthenium(II) hexafluorophosphat;
Dicarbonylcyclopentadienylruthenium(II) dimer;
Dichloro(benzene)ruthenium(II);
Di-μ-chlorobis[(p-cymene)chlororuthenium(II)];
Dichloro(1,5-cyclooctadiene)ruthenium(II);
Dichlorotricarbonylruthenium (dimer);
Dichloro(pentamethylcyclopentadienyl)ruthenium(III) polymer;
Ruthenium(III) acetylacetonate;
Ruthenium(III) bromide;
Ruthenium(III) chloride;
Ruthenium(III) iodide;
Acetatodicarbonylruthenium(IV) polymer;
Ammonium hexachlororuthenate(IV);
Dichloro(μ-chloro)bis[(1,2,3,6,7,8-η)-2,7-dimethyl-2,6-octadien-1,8-diyl]diruthenium(IV); and
Dichloro(2,6,10-dodecatriene-1,12-diyl)ruthenium(IV).

* * * * *